United States Patent
Chen et al.

(12) 
(10) Patent No.: US 6,211,111 B1
(45) Date of Patent: Apr. 3, 2001

(54) ACTIVATOR COMPOSITION COMPRISING ALUMINUM COMPOUND MIXTURE

(75) Inventors: Eugene Y. Chen, Midland; William J. Kruper, Jr., Sanford; Gordon R. Roof, Midland, all of MI (US); David J. Schwartz, Lake Jackson, TX (US); Joey W. Storer, Plymouth, MN (US)

(73) Assignee: The Dow Chemical Company, Midland, MI (US)

( * ) Notice: Subject to any disclaimer, the term of this patent is extended or adjusted under 35 U.S.C. 154(b) by 0 days.

(21) Appl. No.: 09/330,675

(22) Filed: Jun. 11, 1999

Related U.S. Application Data

(60) Provisional application No. 60/096,800, filed on Aug. 17, 1998, now abandoned, and provisional application No. 60/100,490, filed on Sep. 16, 1998, now abandoned.

(51) Int. Cl.$^7$ ............................................. B01J 31/00
(52) U.S. Cl. ........................... 502/152; 502/153; 502/154
(58) Field of Search .............................. 502/152, 153, 502/154

(56) References Cited

U.S. PATENT DOCUMENTS

| | | | |
|---|---|---|---|
| 5,387,568 | * | 2/1995 | Ewen et al. ............................ 502/152 |
| 5,470,993 | | 11/1995 | Devore et al. . |
| 5,599,761 | * | 2/1997 | Turner .................................. 502/152 |
| 5,602,269 | | 2/1997 | Biagini et al. . |
| 5,854,166 | * | 12/1998 | Marks et al. ........................... 502/153 |
| 5,856,258 | * | 1/1999 | Marks et al. ........................... 502/152 |
| 5,895,771 | * | 4/1999 | Epstein et al. ......................... 502/152 |
| 6,046,347 | * | 4/2000 | Jones et al. ........................... 502/152 |
| 6,130,302 | * | 10/2000 | Marks et al. ........................... 502/153 |
| 6,147,174 | * | 4/2000 | Holtcamp et al. ...................... 502/153 |

FOREIGN PATENT DOCUMENTS

| | | | |
|---|---|---|---|
| 504329 | * | 7/1983 | (SU) .................................... 502/152 |
| 97/27228 | | 7/1997 | (WO) . |
| 98/03558 | | 1/1998 | (WO) . |

OTHER PUBLICATIONS

Ewen, *Stud. In Surf. Sci. Catal.*, 89, 405–410, (1994).
Bochmann et al., (ACS Dallas Meeting, Mar. 1998, ABS. No. INOR 264, subsequently published, *Organometallics,* 1998, 17, 5908–5912).

* cited by examiner

Primary Examiner—Mark L. Bell
Assistant Examiner—J. Pasterczyk

(57) ABSTRACT

Compositions comprising:

A) an aluminum compound corresponding to the formula $AlAr^f_3$, where $Ar^f$ is a fluorinated aromatic hydrocarbyl moiety of from 6 to 30 carbon atoms;

B) an aluminum compound corresponding to the formula: $AlAr^fQ^1Q^2$, or a dimer, adduct, or mixture thereof; where:

$Ar^f$ is as previously defined;

$Q^1$ is $Ar^f$ or a $C_{1-20}$ hydrocarbyl group, optionally substituted with one or more cyclohydrocarbyl, hydrocarbyloxy, hydrocarbylsiloxy, hydrocarbylsilylamino, hydrocarbylsilyl, silylhydrocarbyl, di(hydrocarbylsilyl)amino, hydrocarbylamino, di(hydrocarbyl)amino, di(hydrocarbyl)phosphino, or hydrocarbylsulfido groups having from 1 to 20 atoms other than hydrogen, or, further optionally, such substituents may be covalently linked with each other to form one or more fused rings or ring systems; and $Q^2$ is an aryloxy, arylsulfide or di(hydrocarbyl)amido group, optionally substituted with one or more hydrocarbyl, cyclohydrocarbyl, hydrocarbyloxy, hydrocarbylsiloxy, hydrocarbylsilylamino, hydrocarbylsilyl, silylhydrocarbyl, di(hydrocarbylsilyl)amino, hydrocarbylamino, di(hydrocarbyl)amino, di(hydrocarbyl)phosphino, or hydrocarbylsulfido groups having from 1 to 20 atoms other than hydrogen, or, further optionally such substituents may be covalently linked with each other to form one or more fused rings or ring systems, said $Q^2$ having from 3 to 20 atoms other than hydrogen; and the molar ratio of A):B) in the composition being from 0.1:1 to 10:1 are useful as activators for olefin polymerizations.

4 Claims, No Drawings

ACTIVATOR COMPOSITION COMPRISING ALUMINUM COMPOUND MIXTURE

CROSS-REFERENCE TO RELATED APPLICATION

This application claims benefit of priority from provisional applications 60/096,800, filed Aug. 17, 1998 and 60/100,490, filed Sep. 16, 1998 abn.

BACKGROUND OF THE INVENTION

The present invention relates to compositions that are useful as catalyst activators for olefin polymerizations. More particularly the present invention relates to such compositions that are particularly adapted for use in the coordination polymerization of unsaturated compounds having improved activation efficiency and performance. Such compositions are particularly advantageous for use in a polymerization process wherein catalyst, catalyst activator, and at least one polymerizable monomer are combined under polymerization conditions to form a polymeric product.

It is previously known in the art to activate Ziegler-Natta polymerization catalysts, particularly such catalysts comprising Group 3–10 metal complexes containing delocalized π-bonded ligand groups, by the use of an activator. Generally in the absence of such an activator compound, also referred to as a cocatalyst, little or no polymerization activity is observed.

A class of suitable activators are Lewis acids, especially alumoxanes, which are generally believed to be oligomeric or polymeric alkylaluminoxy compounds, including cyclic oligomers. Examples of alumoxanes (also known as aluminoxanes) include methylalumoxane (MAO) made by hydrolysis of trimethylaluminum as well as modified methylalumoxane (MMAO), wherein a portion of the trimethylaluminum in the foregoing hydrolysis is replaced by a higher trialkylaluminum compound such as triisobutyl-aluminum. MMAO advantageously is more soluble in aliphatic solvents than is MAO.

Generally alumoxanes contain on average about 1.5 alkyl groups per aluminum atom, and are prepared by reaction of trialkylaluminum compounds or mixtures of compounds with water (Reddy et al, *Prog. Poly. Sci.*, 1995, 20, 309–367). The resulting product is in fact a mixture of various substituted aluminum compounds including especially, trialklyaluminum compounds (resulting from incomplete reaction of the trialkylaluminum starting reagent or decomposition of the alumoxane). The amount of such free trialkylaluminum compound in the mixture generally varies from 1 to 50 percent by weight of the total product.

Although effective in forming an active olefin polymerization catalyst when combined with a variety of Group 3–10 metal complexes, especially Group 4 metal complexes, generally a large excess of alumoxane compared to metal complex, such as, molar ratios from 100:1 to 10,000:1, is required in order to produce adequate rates of polymerization. Unfortunately, the use of such large excesses of cocatalyst is expensive and also results in polymer having an elevated residual aluminum content as well as lower molecular weight. This former factor may adversely affect polymer properties, especially clarity and dielectric constant, whereas the latter issue relates to poor polymer performance.

Other types of monomeric aryloxyaluminum and arylamidoaluminum complexes have been found to be useful in metallocene catalyst activator packages, particularly as water and oxygenate scavengers. Examples include diisobutyl-2,6-di-t-butyl-4-methylphenoxyaluminum (DIBAL-BOT) as described in WO 97/27228, or diisobutylhexamethyidisilylazayl aluminum (DIBAL-NS) as described by Rosen et al in WO 98/03558. Typically in such formulations, the Lewis acid, especially tris(pentafluorophanyl)borane, is first contacted with a metal complex to prepare the catalytically activated derivative. Thereafter, this derivative is generally not subject to ligand transfer with the aluminum compound.

A different type of activator compound is a Bronsted acid salt capable of transferring a proton to form a cationic derivative or other catalytically active derivative of such Group 3–10 metal complex, cationic charge transferring compounds, or cationic oxidizing activators, referred to collectively hereinafter as cationic activators. Preferred cationic activators are ammonium, sulfonium, phosphonium, oxonium, ferrocenium, silver, lead, carbonium or silylium compounds containing a cation/ anion pair that is capable of rendering the Group 3–10 metal complex catalytically active. Preferred anions associated with this cation comprise fluorinated arylborate anions, more preferably, the tetrakis(pentafluorophenyl)borate anion. Additional suitable anions include sterically shielded, bridged diboron anions. Examples of such cationic activators are disclosed in U.S. Pat. Nos. 5,198,401, 5,132,380, 5,470,927, 5,153,157, 5,350,723, 5,189,192, 5,626,087 and in U.S. Pat. No. 5,447,895.

Further suitable activators for activating metal complexes for olefin polymerization include neutral Lewis acids such as tris(perfluorophenyl)borane and tris(perfluorobiphenyl)borane. The former composition has been previously disclosed for the above stated end use in U.S. Pat. No. 5,721,185, and elsewhere, whereas the latter composition is disclosed in Marks, et al, *J. Am. Chem. Soc.* 1996, 118, 12451–12452. Additional teachings of the foregoing activators may be found in Chen, et al, *J. Am. Chem. Soc.* 1997, 119, 2582–2583, Jia et al, *Organometallics,* 1997, 16, 842–857, and Coles et al, *J. Am. Chem. Soc.* 1997, 119, 8126—8126.

Tris(perfluorophenyl)aluminum is a strong Lewis acid as well. It has recently been prepared from the exchange of tris(perfluorophenyl)borane with trialkylaluminum, as described by Biagini et al U.S. Pat. No. 5,602,269. However, it generally performs poorly by itself as a catalyst activator compared with tris(perfluorophenyl)borane. Similarly, It has further been demonstrated that active catalysts resulting from the use of an aluminate anion based upon tris-(perfluorophenyl)aluminum for the activation of ansa-metallocenes and biscyclopentadienyl derivatives of zirconium(IV) are generally of lower activity than those formed by the corresponding borane (Ewen, *Stud. in Surf. Sci. Catal.* 1994, 89, 405–410). A possible explanation for the poor performance of tris(perfluorophenyl)aluminum as an activator for metallocenes involving a back exchange reaction of a perfluorophenyl group has been proposed by Bochmann et al (ACS Dallas Meeting, March 1998, Abs. number INOR 264, subsequently published, *Organometallics,* 1998, 17, 5908–5912).

In light of these apparent deficiencies, it would be desirable to provide novel compositions having improved efficiency and operability as activators of metal complexes for olefin polymerizations.

SUMMARY OF THE INVENTION

According to the present invention there is now provided a composition comprising:

A) an aluminum compound corresponding to the formula AlAr$^f_3$, where

Ar$^f$ is a fluorinated aromatic hydrocarbyl moiety of from 6 to 30 carbon atoms;

B) an aluminum compound corresponding to the formula: AlAr$^f$Q$^1$Q$^2$, or a dimer, adduct, or mixture thereof; where:

Ar$^f$ is as previously defined;

Q$^1$ is Ar$^f$ or a C$_{1-20}$ hydrocarbyl group, optionally substituted with one or more cyclohydrocarbyl, hydrocarbyloxy, hydrocarbylsiloxy, hydrocarbylsilylamino, hydrocarbylsilyl, silylhydrocarbyl, di(hydrocarbylsilyl)amino, hydrocarbylamino, di(hydrocarbyl)amino, di(hydrocarbyl)phosphino, or hydrocarbylsulfido groups having from 1 to 20 atoms other than hydrogen, or, further optionally, such substituents may be covalently linked with each other to form one or more fused rings or ring systems; and Q$^2$ is an aryloxy, arylsulfide or di(hydrocarbyl)amido group, optionally substituted with one or more hydrocarbyl, cyclohydrocarbyl, hydrocarbyloxy, hydrocarbylsiloxy, hydrocarbylsilylamino, hydrocarbylsilyl, silylhydrocarbyl, di(hydrocarbylsilyl)amino, hydrocarbylamino, di(hydrocarbyl)amino, di(hydrocarbyl)phosphino, or hydrocarbylsulfido groups having from 1 to 20 atoms other than hydrogen, or, further optionally such substituents may be covalently linked with each other to form one or more fused rings or ring systems, said Q$^2$ having from 3 to 20 atoms other than hydrogen; and the molar ratio of A):B) in the composition being from 0.1:1 to 10:1, preferably from 1:1 to 8:1, more preferably from 1.5:1 to 5:1.

The subject invention further provides a catalyst composition for polymerization of olefins comprising a Group 3–10 metal complex and an activator comprising the above described composition, the molar ratio of metal complex to activator in the composition being from 0.1:1 to 3:1.

The subject invention further provides a process for the polymerization of one or more addition polymerizable monomers comprising contacting one or more addition polymerizable monomers under addition polymerization conditions with the catalyst composition as described above.

The compounds are capable of forming unique bis μ-bridged adducts with Group 4 metal complexes, i.e., compounds that are essentially doubly activated, that are useful addition polymerization catalysts.

DETAILED DESCRIPTION

All references herein to elements belonging to a certain Group refer to the Periodic Table of the Elements published and copyrighted by CRC Press, Inc., 1995. Also any reference to the Group or Groups shall be to the Group or Groups as reflected in this Periodic Table of the Elements using the IUPAC system for numbering groups. Where any reference is made herein to any publication, patent application or provisional patent application, the contents thereof are incorporated herein in its entirety by reference.

Preferred compositions according to the present invention are those wherein Ar$^f$ is a perfluoroaryl group, more preferably a perfluorophenyl group, Q$^1$ is C$_{3-6}$ alkyl containing at least one secondary or tertiary carbon center, more preferably isopropyl or isobutyl, and Q$^2$ is aryloxy or dialkylamido of up to 10 carbons, more preferably 2,6-ditert-butylphenoxy, 2,6-ditert-butyl-4-methylphenoxy, N,N-bis(trimethylsilyl)amido, or N,N-dimethylamido. Most preferred compounds are monomers, rather than dimers or adducts.

A most preferred compound B) for use according to the invention is isobutylperfluorophenyl-2-methyl-4,6-di-t-butylphenoxyaluminum or isobutylperfluorophenyl-4,6-di-t-butylphenoxyaluminum.

The compounds of formula B) are readily prepared by contacting under ligand exchange reaction conditions a trifluoroarylaluminum compound of the formula AlAr$^f_3$, wherein Ar$^f$ is as previously defined, with a Group 13 organometallic compound of the formula: Q$^3_2$Me$^2$Q$^2$, wherein Q$^2$ is as previously defined;

Q$^3$ is independently each occurrence C$_{1-4}$ alkyl; and

Me$^2$ is a Group 13 metal, preferably aluminum.

Preferably the exchange reaction is conducted in an aliphatic, cycloaliphatic or aromatic hydrocarbon liquid or mixture thereof under anhydrous conditions. Further preferably, the trifluoroaryl aluminum compound is provided in greater than a stoichiometric amount with respect to the Group 13 organometallic compound, more preferably at a molar ratio from 1.5:1 to 20:1, most preferably from 2:1 to 10:1. Preferred are the use of solutions of the foregoing reactants in concentrations of trifluoroarylaluminum compound and Group 13 organometallic compound from 0.005 to 2M, preferably from 0.02 to 1.5 M, and most preferably from 0.05 to 1.2 M. Generally, the Group 13 organometallic compound readily transfers one Q$^3$ group. However, the rate of transfer of a second Q$^3$ group is kinetically disfavored, thereby allowing for the preparation of mixtures of the desired components A) and B) in high yield and efficiency.

The rate of ligand exchange can be enhanced by heating the reaction mixture or by removing any alkyl exchange byproducts in the reaction mixture. A preferred temperature range for the exchange reaction is from 0 to 50° C., more preferably from 15 to 35° C. Suitable techniques for removing alkyl exchange byproducts from the reaction mixture include degassing optionally at reduced pressures, distillation, solvent exchange, solvent extraction, extraction with a volatile agent, contacting with a zeolite or molecular sieve, and combinations of the foregoing techniques, all of which are conducted according to conventional procedures. Purity of the resulting product may be determined by analysis of the resulting product. Removal of volatile by-products will assist in shifting the equilibrium concentration of desired end products. Generally, reaction times from 10 minutes to 6 hours, preferably 15 minutes to 1 hour are used to ensure formation of the desired ligand exchange products.

In as much as the compounds of formula B) are desirably prepared by an exchange reaction as previously described, it is to be understood that additional components of the reaction mixture may include alternative exchange products, such as multiple compounds corresponding to the formula, AlAr$^f$Q$^1$Q$^2$, as well as compounds of the formula AlAr$^f$Q$^1_2$ wherein at least one Q$^1$ group is not Ar$^f$. A particularly preferred embodiment of the invention is a composition comprising:

A) an aluminum compound corresponding to the formula AlAr$^f_3$, where

Ar$^f$ is a fluorinated aromatic hydrocarbyl moiety of from 6 to 30 carbon atoms;

B) an aluminum compound corresponding to the formula: AlAr$^f$Q$^1$Q$^2$, or a dimer, adduct, or mixture thereof; where:

Ar$^f$ is as previously defined;

Q$^1$ is Ar$^f$ or a C$_{1-20}$ hydrocarbyl group, optionally substituted with one or more cyclohydrocarbyl, hydrocarbyloxy, hydrocarbylsiloxy, hydrocarbylsilylamino, hydrocarbylsilyl, silylhydrocarbyl, di(hydrocarbylsilyl)

amino, hydrocarbylamino, di(hydrocarbyl)amino, di(hydrocarbyl)phosphino, or hydrocarbylsulfido groups having from 1 to 20 atoms other than hydrogen, or, further optionally, such substituents may be covalently linked with each other to form one or more fused rings or ring systems;

$Q^2$ is an aryloxy, arylsulfide or di(hydrocarbyl)amido group, optionally substituted with one or more hydrocarbyl, cyclohydrocarbyl, hydrocarbyloxy, hydrocarbylsiloxy, hydrocarbylsilylamino, hydrocarbylsilyl, silylhydrocarbyl, di(hydrocarbylsilyl)amino, hydrocarbylamino, di(hydrocarbyl)amino, di(hydrocarbyl)phosphino, or hydrocarbylsulfido groups having from 1 to 20 atoms other than hydrogen, or, further optionally such substituents may be covalently linked with each other to form one or more fused rings or ring systems, said $Q^2$ having from 3 to 20 atoms other than hydrogen; and C) an aluminum exchange compound or mixture thereof, in the aggregate corresponding to the formula, $AlAr^f_2Q^1$, wherein $Q^1$ is not $Ar^f$, the molar ratio of A):B):C) in the composition being from 0.1:1.0:0.001 to 10.0:1.0:1.0, preferably from 1.0:1.0:0.01 to 8.0:1.0:1.0, more preferably from 1.5:1:0.01 to 5.0:1.0:1.0.

The present mixture of compounds in the indicated molar ratio provides highly active co-catalysts for use in activation of metal complexes, especially Group 4 metallocenes for the polymerization of olefins. When amounts of $AlAr^f_3$ less than the quantity specified are employed, the cocatalytic activity of the mixture is generally reduced. When amounts of $AlAr^f_3$ greater than the quantity specified are employed, no significant improvement in properties results and the excess amount is wasted. It is to be further understood that the moieties A), B) and C) may exist as discreet entities or as dynamic exchange products. In addition, additional minor exchange products may also be formed in the foregoing exchange reaction. These additional exchange products do not affect the performance of the present compositions. When used as a cocatalyst, the mixture desirably is employed as a dilute solution in a hydrocarbon liquid, especially an aliphatic hydrocarbon liquid for use as a homogeneous catalyst, especially solution polymerizations. Additionally, the composition may be deposited on an inert support, especially a particulated metal oxide or polymer, in combination with the metal complex to be activated according to known techniques for producing supported olefin polymerization catalysts, and thereafter used for gas phase or slurry polymerizations.

When in use as a catalyst activator, the molar ratio of metal complex to activator composition is preferably from 0.1:1 to 3:1, more preferably from 0.2:1 to 2:1, most preferably from 0.25:1 to 1:1, based on the metal contents of each component. In most polymerization reactions, the molar ratio of metal complex: polymerizable compound employed is from $10^{-12}:1$ to $10^{-1}:1$, more preferably from $10^{-12}:1$ to $10^{-5}:1$.

The support for the activator component may be any inert, particulated material, but most suitably is a metal oxide or mixture of metal oxides, preferably alumina, silica, an aluminosilicate or clay material. Suitable volume average particle sizes of the support are from 1 to 1000 $\mu$M, preferably from 10 to 100 $\mu$M. Most desired supports are calcined silica, which may be treated prior to use to reduce surface hydroxyl groups thereon, by reaction with a silane, a trialkylaluminum, or similar reactive compound. Any suitable means for incorporating the perfluoroarylaluminum containing co-catalyst mixture onto the surface of a support may be used, including dispersing the co-catalyst in a liquid and contacting the same with the support by slurrying, impregnation, spraying, or coating and thereafter removing the liquid, or by combining the cocatalyst and a support material in dry or paste form and intimately contacting the mixture, thereafter forming a dried, particulated product.

Suitable metal complexes for use in combination with the foregoing cocatalysts include any complex of a metal of Groups 3–10 of the Periodic table of the Elements capable of being activated to polymerize addition polymerizable compounds, especially olefins by the present activators. Examples include Group 10 diimine derivatives corresponding to the formula:

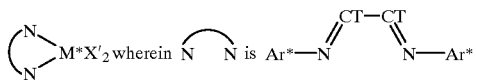

$M^*$ is Ni(II) or Pd(II);

X' is halo, hydrocarbyl, or hydrocarbyloxy;

$Ar^*$ is an aryl group, especially 2,6-diisopropylphenyl or aniline group; and

CT-CT is 1,2-ethanediyl, 2,3-butanediyl, or form a fused ring system wherein the two T groups together are a 1,8-naphthanediyl group.

Similar complexes to the foregoing are disclosed by M. Brookhart, et al., in *J. Am. Chem. Soc.*, 118, 267–268 (1996) and *J. Am. Chem. Soc.*, 117, 6414–6415 (1995), as being suitable for forming active polymerization catalysts especially for polymerization of $\alpha$-olefins, either alone or in combination with polar comonomers such as vinyl chloride, alkyl acrylates and alkyl methacrylates.

Additional complexes include derivatives of Group 3, 4, or Lanthanide metals containing from 1 to 3 $\pi$-bonded anionic or neutral ligand groups, which may be cyclic or non-cyclic delocalized $\pi$-bonded anionic ligand groups. Exemplary of such $\pi$-bonded anionic ligand groups are conjugated or nonconjugated, cyclic or non-cyclic dienyl groups, allyl groups, boratabenzene groups, and arene groups. By the term "$\pi$-bonded" is meant that the ligand group is bonded to the transition metal by a sharing of electrons from a delocalized $\pi$-bond.

Each atom in the delocalized $\pi$-bonded group may independently be substituted with a radical selected from the group consisting of hydrogen, halogen, hydrocarbyl, halohydrocarbyl, hydrocarbyloxy, hydrocarbylsulfide, dihydrocarbylamino, and hydrocarbyl-substituted metalloid radicals wherein the metalloid is selected from Group 14 of the Periodic Table of the Elements, and such hydrocarbyl-, halohydrocarbyl-, hydrocarbyloxy-, hydrocarbylsulfide-, dihydrocarbylamino- or hydrocarbyl-substituted metalloid-radicals that are further substituted with a Group 15 or 16 hetero atom containing moiety. Included within the term "hydrocarbyl" are $C_{1-20}$ straight, branched and cyclic alkyl radicals, $C_{6-20}$ aromatic radicals, $C_{7-20}$ alkyl-substituted aromatic radicals, and $C_{7-20}$ aryl-substituted alkyl radicals. In addition two or more such radicals may together form a fused ring system, including partially or fully hydrogenated fused ring systems, or they may form a metallocycle with the metal. Suitable hydrocarbyl-substituted organometalloid radicals include mono-, di- and tri-substituted organometalloid radicals of Group 14 elements wherein each of the hydrocarbyl groups contains from 1 to 20 carbon atoms. Examples of suitable hydrocarbyl-substituted organometalloid radicals include trimethylsilyl, triethylsilyl, ethyldimethylsilyl, methyldiethylsilyl, triphenylgermyl, and trimethylgermyl groups. Examples of Group 15 or 16 hetero atom containing moieties include amine, phosphine, ether or thioether moieties or divalent derivatives thereof, for example amide, phosphide, ether or thioether groups bonded to the transition metal or Lanthanide metal, and bonded to the hydrocarbyl group or to the hydrocarbyl- substituted metalloid containing group.

Examples of suitable anionic, delocalized π-bonded groups include cyclopentadienyl, indenyl, fluorenyl, tetrahydroindenyl, tetrahydrofluorenyl, octahydrofluorenyl, pentadienyl, cyclohexadienyl, dihydroanthracenyl, hexahydroanthracenyl, decahydroanthracenyl groups, and boratabenzene groups, as well as $C_{1-10}$ hydrocarbyl-substituted, $C_{1-10}$ hydrocarbyloxy- substituted, di($C_{1-10}$ hydrocarbyl)amino- substituted, or tri($C_{1-10}$ hydrocarbyl) silyl- substituted derivatives thereof. Preferred anionic delocalized π-bonded groups are cyclopentadienyl, pentamethylcyclopentadienyl, tetramethylcyclopentadienyl, tetramethylsilylcyclopentadienyl, indenyl, 2,3-dimethylindenyl, fluorenyl, 2-methylindenyl, 2-methyl-4-phenylindenyl, tetrahydrofluorenyl, octahydrofluorenyl, and tetrahydroindenyl.

The boratabenzenes are anionic ligands which are boron containing analogues to benzene. They are previously known in the art having been described by G. Herberich, et al., in *Organometallics*, 1995, 14, 1, 471–480. Preferred boratabenzenes correspond to the formula:

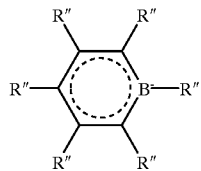

wherein R'' is selected from the group consisting of hydrocarbyl, silyl, or germyl, said R'' having up to 20 non-hydrogen atoms. In complexes involving divalent derivatives of such delocalized π-bonded groups one atom thereof is bonded by means of a covalent bond or a covalently bonded divalent group to another atom of the complex thereby forming a bridged system.

Suitable metal complexes for use in the catalysts of the present invention may be derivatives of any transition metal including Lanthanides, but preferably of Group 3, 4, or Lanthanide metals which are in the +2, +3, or +4 formal oxidation state meeting the previously mentioned requirements. Preferred compounds include metal complexes (metallocenes) containing from 1 to 3 π-bonded anionic ligand groups, which may be cyclic or noncyclic delocalized π-bonded anionic ligand groups. Exemplary of such π-bonded anionic ligand groups are conjugated or nonconjugated, cyclic or non-cyclic dienyl groups, allyl groups, and arene groups. By the term "π-bonded" is meant that the ligand group is bonded to the transition metal by means of delocalized electrons present in a π bond.

Examples of suitable anionic, delocalized π-bonded groups include cyclopentadienyl, indenyl, fluorenyl, tetrahydroindenyl, tetrahydrofluorenyl, octahydrofluorenyl, pentadienyl, cyclohexadienyl, dihydroanthracenyl, hexahydroanthracenyl, and decahydroanthracenyl groups, as well as $C_{1-10}$ hydrocarbyl-substituted derivatives thereof. Preferred anionic delocalized π-bonded groups are cyclopentadienyl, pentamethylcyclopentadienyl, tetramethylcyclopentadienyl, indenyl, 2,3-dimethylindenyl, fluorenyl, 2-methylindenyl and 2-methyl-4-phenylindenyl.

More preferred are metal complexes corresponding to the formula:

or a dimer thereof wherein:

L is an anionic, delocalized, π-bonded group that is bound to M, containing up to 50 atoms not counting hydrogen, optionally two L groups may be joined together through one or more substituents thereby forming a bridged structure, and further optionally one L may be bound to X through one or more substituents of L;

M is a metal of Group 4 of the Periodic Table of the Elements in the +2, +3 or +4 formal oxidation state;

X is an optional, divalent substituent of up to 50 non-hydrogen atoms that together with L forms a metallocycle with M;

X' is an optional neutral Lewis base having up to 20 non-hydrogen atoms;

X'' each occurrence is a monovalent, anionic moiety having up to 40 non-hydrogen atoms, optionally, two X'' groups may be covalently bound together forming a divalent dianionic moiety having both valences bound to M, or form a neutral, conjugated or nonconjugated diene that is π-bonded to M (whereupon M is in the +2 oxidation state), or further optionally one or more X'' and one or more X' groups may be bonded together thereby forming a moiety that is both covalently bound to M and coordinated thereto by means of Lewis base functionality;

l is 1 or 2;

m is 0 or 1;

n is a number from 0 to 3;

p is an integer from 0 to 3; and the sum, l+m+p, is equal to the formal oxidation state of M.

Such preferred complexes include those containing either one or two L groups. The latter complexes include those containing a bridging group linking the two L groups. Preferred bridging groups are those corresponding to the formula $(ER*_2)_x$ wherein E is silicon or carbon, R* independently each occurrence is hydrogen or a group selected from silyl, hydrocarbyl, hydrocarbyloxy and combinations thereof, said R* having up to 30 carbon or silicon atoms, and x is 1 to 8. Preferably, R* independently each occurrence is methyl, benzyl, tert-butyl or phenyl.

Examples of the foregoing bis(L) containing complexes are compounds corresponding to the formula:

(I)

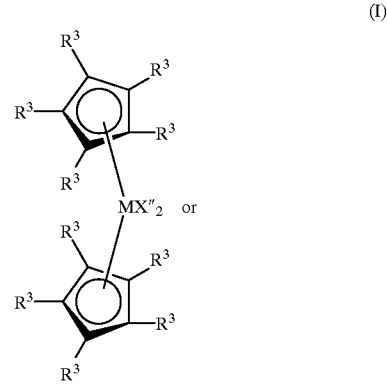

-continued (II)

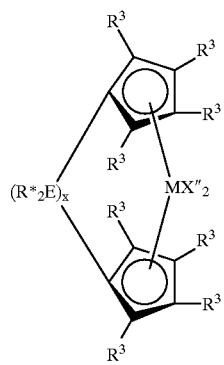

wherein:

M is titanium, zirconium or hafnium, preferably zirconium or hafnium, in the +2 or +4 formal oxidation state;

$R^3$ in each occurrence independently is selected from the group consisting of hydrogen, hydrocarbyl, dihydrocarbylamino, hydrocarbyleneamino, silyl, germyl, cyano, halo and combinations thereof, said $R^3$ having up to 20 atoms not counting hydrogen, or adjacent $R^3$ groups together form a divalent derivative thereby forming a fused ring system, and X" independently each occurrence is an anionic ligand group of up to 40 atoms not counting hydrogen, or two X" groups together form a divalent anionic ligand group of up to 40 atoms not counting hydrogen or together are a conjugated diene having from 4 to 30 atoms not counting hydrogen forming a π-complex with M, whereupon M is in the +2 formal oxidation state, and R*, E and x are as previously defined.

The foregoing metal complexes are especially suited for the preparation of polymers having stereoregular molecular structure. In such capacity it is preferred that the complex possess $C_2$ symmetry or possess a chiral, stereorigid structure. Examples of the first type are compounds possessing different delocalized π-bonded systems, such as one cyclopentadienyl group and one fluorenyl group. Similar systems based on Ti(IV) or Zr(IV) were disclosed for preparation of syndiotactic olefin polymers in Ewen, et al., *J. Am. Chem. Soc.* 110, 6255–6256 (1980). Examples of chiral structures include bis-indenyl complexes. Similar systems based on Ti(IV) or Zr(IV) were disclosed for preparation of isotactic olefin polymers in Wild et al., *J. Organomet. Chem*, 232, 233-47, (1982).

Exemplary bridged ligands containing two π-bonded groups are: (dimethylsilyl-bis-cyclopentadienyl), (dimethylsilyl-bis-methylcyclopentadienyl), (dimethylsilyl-bis-ethylcyclopentadienyl, (dimethylsilyl-bis-t-butylcyclopentadienyl), (dimethylsilyl-bis-tetramethylcyclopentadienyl), (dimethylsilyl-bis-indenyl), (dimethylsilyl-bis-tetrahydroindenyl), (dimethylsilyl-bis-fluorenyl), (dimethylsilyl-bis-tetrahydrofluorenyl), (dimethylsilyl-bis-2-methyl-4-phenylindenyl), (dimethylsilyl-bis-2-methylindenyl), (dimethylsilyl-cyclopentadienyl-fluorenyl), (1,1,2,2-tetramethyl-1,2-disilyl-bis-cyclopentadienyl), (1,2-bis(cyclopentadienyl) ethane, and (isopropylidene-cyclopentadienyl-fluorenyl).

Preferred X" groups are selected from hydride, hydrocarbyl, silyl, germyl, halohydrocarbyl, halosilyl, silylhydrocarbyl and aminohydrocarbyl groups, or two X" groups together form a divalent derivative of a conjugated diene or else together they form a neutral, π-bonded, conjugated diene. Most preferred X" groups are $C_{1-20}$ hydrocarbyl groups.

A further class of metal complexes utilized in the present invention correspond to the formula:

$$L_lMX_mX'_nX''_p,$$

or a dimer thereof
wherein:

L is an anionic, delocalized, π-bonded group that is bound to M, containing up to 50 atoms not counting hydrogen;

M is a metal of Group 4 of the Periodic Table of the Elements in the +2, +3 or +4 formal oxidation state;

X is a divalent substituent of up to 50 non-hydrogen atoms that together with L forms a metallocycle with M;

X' is an optional neutral Lewis base ligand having up to 20 non-hydrogen atoms;

X" each occurrence is a monovalent, anionic moiety having up to 20 non-hydrogen atoms, optionally two X" groups together may form a divalent anionic moiety having both valences bound to M or a neutral $C_{5-30}$ conjugated diene, and further optionally X' and X" may be bonded together thereby forming a moiety that is both covalently bound to M and coordinated thereto by means of Lewis base functionality;

l is 1 or 2;

m is 1;

n is a number from 0 to 3;

p is an integer from 1 to 2; and the sum, l+m+p, is equal to the formal oxidation state of M.

Preferred divalent X substituents preferably include groups containing up to 30 atoms not counting hydrogen and comprising at least one atom that is oxygen, sulfur, boron or a member of Group 14 of the Periodic Table of the Elements directly attached to the delocalized π-bonded group, and a different atom, selected from the group consisting of nitrogen, phosphorus, oxygen or sulfur that is covalently bonded to M.

A preferred class of such Group 4 metal coordination complexes used according to the present invention correspond to the formula:

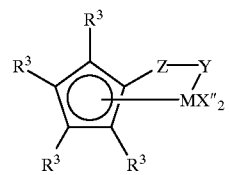

wherein:

M is titanium or zirconium in the +2, +3 or +4 formal oxidation state;

$R^3$ in each occurrence independently is selected from the group consisting of hydrogen, hydrocarbyl, silyl, germyl, cyano, halo and combinations thereof, said $R^3$ having up to 20 non-hydrogen atoms, or adjacent $R^3$ groups together form a divalent derivative (that is, a hydrocarbadiyl, siladiyl or germadiyl group) thereby forming a fused ring system, each X" is a halo, hydrocarbyl, hydrocarbyloxy or silyl group, said group having up to 20 atoms not counting hydrogen, or two X" groups together form a $C_{5-30}$ conjugated diene;

Y is —O—, —S—, —NR*—, —NR*$_2$, —PR*—; and

Z is $SiR*_2$, $CR*_2$, $SiR*_2SiR*_2$, $CR*_2CR*_2$, $CR*{=}CR*$, $CR*_2SiR*_2$, or $GeR*_2$, wherein: R* is as previously defined.

Illustrative Group 4 metal complexes that may be employed in the practice of the present invention include:

cyclopentadienyltitaniumtrimethyl,
cyclopentadienyltitaniumtriethyl,
cyclopentadienyltitaniumtriisopropyl,
cyclopentadienyltitaniumtriphenyl,
cyclopentadienyltitaniumtribenzyl,
cyclopentadienyltitanium-2,4-pentadienyl,
(tert-butylamido)(tetramethyl-$\eta^5$-cyclopentadienyl) dimethylsilanetitanium dimethyl,
(tert-butylamido)(tetramethyl-$\eta^5$-cyclopentadienyl)-1,2-ethanediyltitanium dimethyl,
(tert-butylamido)(hexamethyl-$\eta^5$-indenyl) dimethylsilanetitanium dimethyl,
(tert-butylamido)(tetramethyl-$\eta^5$-cyclopentadienyl) dimethylsilane titanium (III) 2-(dimethylamino)benzyl;
(tert-butylamido)(tetramethyl-$\eta^5$-cyclopentadienyl) dimethylsilanetitanium (III) allyl,
(tert-butylamido)(tetramethyl-$\eta^5$-cyclopentadienyl) dimethylsilanetitanium (II) 1,4-diphenyl-1,3-butadiene,
(tert-butylamido)(2-methylindenyl)dimethylsilanetitanium (II)1,4-diphenyl-1,3-butadiene,
(tert-butylamido)(2-methylindenyl)dimethylsilanetitanium (IV) 1,3-butadiene,
(tert-butylamido)(2,3-dimethylindenyl) dimethylsilanetitanium (II) 1,4-diphenyl-1,3-butadiene,
(tert-butylamido)(2,3-dimethylindenyl) dimethylsilanetitanium (IV) 1,3-butadiene,
(tert-butylamido)(2,3-dimethylindenyl) dimethylsilanetitanium (II) 1,3-pentadiene,
(tert-butylamido)(2-methylindenyl)dimethylsilanetitanium (II) 1,3-pentadiene,
(tert-butylamido)(2-methylindenyl)dimethylsilanetitanium (IV) dimethyl,
(tert-butylamido)(2-methyl-4-phenylindenyl) dimethylsilanetitanium (II) 1,4-diphenyl-1,3-butadiene,
(tert-butylamido)(tetramethyl-$\eta^5$-cyclopentadienyl) dimethylsilanetitanium (IV) 1,3-butadiene,
(tert-butylamido)(tetramethyl-$\eta^5$-cyclopentadienyl) dimethylsilanetitanium (II) 1,4-dibenzyl-1,3-butadiene,
(tert-butylamido)(tetramethyl-$\eta^5$-cyclopentadienyl) dimethylsilanetitanium (II) 2,4-hexadiene,
(tert-butylamido)(tetramethyl-$\eta^5$-cyclopentadienyl) dimethylsilanetitanium (II) 3-methyl 1,3-pentadiene,
(tert-butylamido)(2,4-dimethyl-1,3-pentadien-2-yl) dimethylsilanetitaniumdimethyl,
(tert-butylamido)(1,1-dimethyl-2,3,4,9,10-$\eta$-1,4,5,6,7,8-hexahydronaphthalen-4-yl) dimethylsilanetitaniumdimethyl,
(tert-butylamido)(1,1,2,3-tetramethyl-2,3,4,9,10-$\eta$-1,4,5,6,7,8-hexahydronaphthalen-4-yl) dimethylsilanetitaniumdimethyl,
(tert-butylamido)(tetramethylcyclopentadienyl) dimethylsilanetitanium 1,3-pentadiene,
(tert-butylamido)(3-(N-pyrrolidinyl)inden-1-yl) dimethylsilanetitanium 1,3-pentadiene,
(tert-butylamido)(2-methyl-s-indacen-1-yl) dimethylsilanetitanium 1,3-pentadiene, and
(tert-butylamido)(3,4-cyclopenta(/)phenanthren-2-yl) dimethylsilanetitanium 1,4-diphenyl-1,3-butadiene.

Bis(L) containing complexes including bridged complexes suitable for use in the present invention include:

biscyclopentadienylzirconiumdimethyl,
biscyclopentadienylzirconiumdiethyl,
biscyclopentadienylzirconiumdiisopropyl,
biscyclopentadienylzirconiumdiphenyl,
biscyclopentadienylzirconium dibenzyl,
biscyclopentadienylzirconium-2,4-pentadienyl,
biscyclopentadienylzirconiummethylmethoxide,
biscyclopentadienylzirconiummethylchloride,
bispentamethylcyclopentadienylzirconiumdimethyl,
bisindenylzirconiumdimethyl,
indenylfluorenylzirconiumdiethyl,
bisindenylzirconiummethyl(2-(dimethylamino)benzyl),
bisindenylzirconium methyltrimethylsilyl,
bistetrahydroindenylzirconium methyltrimethylsilyl,
bispentamethylcyclopentadienylzirconiumdiisopropyl,
bispentamethylcyclopentadienylzirconiumdibenzyl,
bispentamethylcyclopentadienylzirconiummethylmethoxide,
(dimethylsilyl-bis-cyclopentadienyl)zirconiumdimethyl,
(dimethylsilyl-bis-pentamethylcyclopentadienyl)zirconium-2,4-pentadienyl,
(methylene-bis-pentamethylcyclopentadienyl)zirconium (III) 2-(dimethylamino)benzyl,
(dimethylsilyl-bis-2-methylindenyl)zirconiumdimethyl,
(dimethylsilyl-bis-2-methyl-4-phenylindenyl) zirconiumdimethyl,
(dimethylsilyl-bis-2-methylindenyl)zirconium-1,4-diphenyl-1,3-butadiene,
(dimethylsilyl-bis-2-methyl-4-phenylindenyl)zirconium (II) 1,4-diphenyl-1,3-butadiene,
(dimethylsilyl-bis-tetrahydroindenyl)zirconium(II) 1,4-diphenyl-1,3-butadiene,
(dimethylsilyl-bis-tetrahydrofluorenyl)zirconiumdi (trimethylsilyl),
(isopropylidene)(cyclopentadienyl)(fluorenyl) zirconiumdibenzyl, and
(dimethylsilylpentamethylcyclopentadienylfluorenyl) zirconiumdimethyl.

Suitable addition polymerizable monomers for use with the foregoing novel catalyst compositions include ethylenically unsaturated monomers, acetylenic compounds, conjugated or non-conjugated dienes, and polyenes. Preferred monomers include olefins, for example alpha-olefins having from 2 to 20,000, preferably from 2 to 20, more preferably from 2 to 8 carbon atoms and combinations of two or more of such alpha-olefins. Particularly suitable alpha-oletins include, for example, ethylene, propylene, 1-butene, isobutylene, 1-pentene, 4-methylpentene-1, 1-hexene, 1-heptene, 1-octene, 1-nonene, 1-decene, 1-undecene, 1-dodecene, 1-tridecene, 1-tetradecene, 1-pentadecene, or combinations thereof, as well as long chain vinyl terminated oligomeric or polymeric reaction products formed during the polymerization, and $C_{10-30}$ $\alpha$-olefins specifically added to the reaction mixture in order to produce relatively long chain branches in the resulting polymers. Preferably, the alpha-olefins are ethylene, propylene, 1-butene, 1-pentene, 4-methyl-pentene-1, 1-hexene, 1-octene, and combinations of ethylene and/or propene with one or more other alpha-olefins. Other preferred monomers include styrene, halo- or alkyl substituted styrenes, vinylbenzocyclobutene, 1,4-hexadiene, dicyclopentadiene, ethylidene norbornene, and 1,7-octadiene. Mixtures of the above-mentioned monomers may also be employed.

In general, the polymerization may be accomplished under conditions well known in the prior art for Ziegler-Natta or Kaminsky-Sinn type polymerization reactions. Suspension, solution, slurry, gas phase or high pressure, whether employed in batch or continuous form or other process conditions, may be employed if desired. Examples of such well known polymerization processes are depicted in WO 88/02009, U.S. Pat. Nos. 5,084,534, 5,405,922, 4,588, 790, 5,032,652, 4,543,399, 4,564,647, 4,522,987, and elsewhere. Preferred polymerization temperatures are from 0–250° C. Preferred polymerization pressures are from atmospheric to 3000 atmospheres.

Preferred processing conditions include solution polymerization, more preferably continuous solution polymerization processes, conducted in the presence of an aliphatic or alicyclic liquid diluent. By the term "continuous polymerization" is meant that at least the products of the polymerization are continuously removed from the reaction mixture. Preferably one or more reactants are also continuously added to the polymerization mixture during the polymerization. Examples of suitable aliphatic or alicyclic liquid diluents include straight and branched-chain $C_{4-12}$ hydrocarbons and mixtures thereof; alicyclic hydrocarbons such as cyclohexane, cycloheptane, methylcyclohexane, methylcycloheptane, and mixtures thereof; and perfluorinated hydrocarbons such as perfluorinated $C_{4-10}$ alkanes, and the like. Suitable diluents also include aromatic hydrocarbons (particularly for use with aromatic α-olefins such as styrene or ring alkyl-substituted styrenes) including toluene, ethylbenzene or xylene, as well as liquid olefins (which may act as monomers or comonomers) including ethylene, propylene, 1-butene, isobutylene, butadiene, 1-pentene, cyclopentene, 1-hexene, cyclohexene, 3-methyl-1-pentene, 4-methyl-1-pentene, 1,4-hexadiene, 1-octene, 1-decene, styrene, divinylbenzene, allylbenzene, vinyltoluene (including all isomers alone or in admixture), and the like. Mixtures of the foregoing are also suitable. The foregoing diluents may also be advantageously employed during the synthesis of the metal complexes and catalyst activators of the present invention.

In most polymerization reactions the molar ratio of catalyst: polymerizable compounds employed is from $10^{-12}:1$ to $10^{-1}:1$, more preferably from $10^{-12}:1$ to $10^{-5}:1$.

The catalyst composition of the invention may also be utilized in combination with at least one additional homogeneous or heterogeneous polymerization catalyst in separate reactors connected in series or in parallel to prepare polymer blends having desirable properties. An example of such a process is disclosed in WO 94/00500, equivalent to U.S. Ser. No. 07/904,770. A more specific process is disclosed in copending application U.S. Ser. No. 08/10958, filed Jan. 29, 1993. The teachings of the foregoing publications and pending applications are hereby incorporated by reference.

Molecular weight control agents can be used in combination with the present cocatalysts. Examples of such molecular weight control agents include hydrogen, trialkyl aluminum compounds or other known chain transfer agents. A particular benefit of the use of the present cocatalysts is the ability (depending on reaction conditions) to produce narrow molecular weight distribution α-olefin homopolymers and copolymers in greatly improved catalyst efficiencies. Preferred polymers have Mw/Mn of less than 2.5, more preferably less than 2.3. Such narrow molecular weight distribution polymer products are highly desirable due to improved tensile strength properties.

The catalyst composition of the present invention can also be employed to advantage in the gas phase polymerization and copolymerization of olefins, preferably by supporting the catalyst composition by any suitable technique. Gas phase processes for the polymerization of olefins, especially the homopolymerization and copolymerization of ethylene and propylene, and the copolymerization of ethylene with higher alpha olefins such as, for example, 1-butene, 1-hexene, 4-methyl-1-pentene are well known in the art. Such processes are used commercially on a large scale for the manufacture of high density polyethylene (HDPE), medium density polyethylene (MDPE), linear low density polyethylene (LLDPE) and polypropylene.

The gas phase process employed can be, for example, of the type which employs a mechanically stirred bed or a gas fluidized bed as the polymerization reaction zone. Preferred is the process wherein the polymerization reaction is carried out in a vertical cylindrical polymerization reactor containing a fluidized bed of polymer particles supported above a perforated plate, the fluidization grid, by a flow of fluidization gas.

The gas employed to fluidize the bed comprises the monomer or monomers to be polymerized, and also serves as a heat exchange medium to remove the heat of reaction from the bed. The hot gases emerge from the top of the reactor, normally via a tranquilization zone, also known as a velocity reduction zone, having a wider diameter than the fluidized bed and wherein fine particles entrained in the gas stream have an opportunity to gravitate back into the bed. It can also be advantageous to use a cyclone to remove ultra-fine particles from the hot gas stream. The gas is then normally recycled to the bed by means of a blower or compressor and one or more heat exchangers to strip the gas of the heat of polymerization.

A preferred method of cooling of the bed, in addition to the cooling provided by the cooled recycle gas, is to feed a volatile liquid to the bed to provide an evaporative cooling effect. The volatile liquid employed in this case can be, for example, a volatile inert liquid, for example, a saturated hydrocarbon having about 3 to about 8, preferably 4 to 6, carbon atoms. In the case that the monomer or comonomer itself is a volatile liquid or can be condensed to provide such a liquid, this can be suitably be fed to the bed to provide an evaporative cooling effect. Examples of olefin monomers which can be employed in this manner are olefins containing from about 3 to about eight, preferably from 3 to six carbon atoms. The volatile liquid evaporates in the hot fluidized bed to form gas which mixes with the fluidizing gas. If the volatile liquid is a monomer or comonomer, it may undergo some polymerization in the bed. The evaporated liquid then emerges from the reactor as part of the hot recycle gas, and enters the compression/heat exchange part of the recycle loop. The recycle gas is cooled in the heat exchanger and, if the temperature to which the gas is cooled is below the dew point, liquid will precipitate from the gas. This liquid is desirably recycled continuously to the fluidized bed. It is possible to recycle the precipitated liquid to the bed as liquid droplets carried in the recycle gas stream, as described, for example, in EP-A-89691, U.S. Pat. No. 4,543,399, WO 94/25495 and U.S. Pat. No. 5,352,749, which are hereby incorporated by reference. A particularly preferred method of recycling the liquid to the bed is to separate the liquid from the recycle gas stream and to reinject this liquid directly into the bed, preferably using a method which generates fine droplets of the liquid within the bed. This type of process is described in WO 94/28032, the teachings of which are also hereby incorporated by reference.

The polymerization reaction occurring in the gas fluidized bed is catalyzed by the continuous or semi-continuous addition of catalyst. Such catalyst can be supported on an inorganic or organic support material if desired. The catalyst can also be subjected to a prepolymerization step, for example, by polymerizing a small quantity of olefin monomer in a liquid inert diluent, to provide a catalyst composite comprising catalyst particles embedded in olefin polymer particles.

The polymer is produced directly in the fluidized bed by catalyzed (co)polymerization of the monomer(s) on the fluidized particles of catalyst, supported catalyst or prepolymer within the bed. Start-up of the polymerization reaction is achieved using a bed of preformed polymer particles, which, preferably, is similar to the target polyolefin, and conditioning the bed by drying with a dry inert gas such as nitrogen prior to introducing the catalyst, the monomer(s) and any other gases which it is desired to have in the recycle gas stream, such as a diluent gas, hydrogen chain transfer agent, or an inert condensable gas when operating in gas phase condensing mode. The produced polymer is discharged continuously or discontinuously from the fluidized bed as desired, optionally exposed to a catalyst kill and optionally pelletized.

It is understood that the present invention is operable in the absence of any component which has not been specifically disclosed. The following examples are provided in order to further illustrate the invention and are not to be construed as limiting. Unless stated to the contrary, all parts and percentages are expressed on a weight basis. The term "overnight", if used, refers to a time of approximately 16–18 hours, "room temperature", if used, refers to a temperature of about 20–25° C., and "mixed alkanes" refers to a mixture of hydrogenated propylene oligomers, mostly $C_6$–$C_{12}$ isoalkanes, available commercially under the trademark Isopar E™ from Exxon Chemicals Inc.

EXAMPLES

Tris(perfluorophenyl)borane (FAB) was obtained as a solid from Boulder Scientific Inc. and used without further purification. Modified methalumoxane (MMAO-3A) in heptane was purchased from Akzo-Nobel. MAO and trimethylaluminum (TMA) both in toluene were purchased from Aldrich Chemical Co. Tris(perfluorophenyl)aluminum (FAAL) in toluene was prepared by exchange reaction between tris(perfluorophenyl)borane and trimethylaluminum. All solvents were purified using the technique disclosed by Pangborn et al, *Organometallics*, 1996, 15, 1518–1520. All compounds and solutions were handled under an inert atmosphere (dry box). All chemical shift for $^{19}F$ NMR spectra were relative to a fixed external standard ($CFCl_3$) in benzene $d_6$ or toluene $d_8$, either of which were dried over N/K alloy and filtered prior to use. $^1H$ and $^{13}C$ NMR shifts were referenced to internal solvent resonances and are reported relative to TMS.

Preparation of diisobutyl(2,6-di-t-butyl-4-methylphenoxy)aluminum (DIBAL-BOT) was conducted according to the method of Skowronska-Ptasinska, M. et al., *J. Organometallic Chem.*, 1978, 160, 403–409. The product was isolated as a colorless oil. NMR spectroscopic data are as follows: $^1H$ NMR ($C_6D_6$) δ7.08, 2.27(s,3H), 2.03, m, 1H, J=6.8 Hz), 1.48 (s, 18H), 1.02 (d, 12H, J=6.8 Hz), 0.39 (d, 12H, J=6.8 Hz); $^{13}C$ NMR ($C_6D_6$) δ153.9, 138.1, 127.2, 126.0, 34.8, 32.1, 28.2, 25.8, 24.0, 21.5.

Example 1

In a glove box, FAAL (0.012 g, 0.02 mmol, toluene adduct) and di(isobutyl)(2,6-di-tert-butyl-4-methylphenoxy) aluminum (dibal-bot) (0.007 g, 0.02 mmol) were mixed in 0.7 mL of benzene-$d_6$ and the mixture was loaded into a NMR tube. NMR spectra were recorded after mixing these reagents in the NMR tube for 10 min. Two new species: isobutylpentafluorophenyl(2,4-di-tert-butyl-4-methylphenoxy)aluminum, and isobutylbis(pentafluorophenyl)aluminum were found to form from the exchange. No significant spectroscopic changes in products or ratios of products were found after 4 h.

iBu($C_6F_5$)Al(BHT) $^1H$ NMR ($C_6D_6$, 23° C.): δ7.10 (s, 2 H, Ar), 2.25 (s, 3 H, Ar-$CH_3$), 1.89 (septet, $J_{H–H}$=6.6 Hz, 1H, $Me_2CHCH_2$—), 1.50 (s, 18 H, tBu), 0.89 (d, $J_{H–H}$=6.6 Hz, 6 H, $Me_2CHCH_2$—), 0.50 (d, $J_{H–H}$=7.2 Hz, 2 H, $Me_2CHCH_2$—). $^{19}F$ NMR ($C_6D_6$, 23° C.): δ−120.93 (dd, $^3J_{F–F}$=18.3 Hz, 2 F, o-F), −149.65 (t, $^3J_{F–F}$=21.4 Hz, 1F, p F), −159.61 (tt, $^3J_{F–F}$=24.5 Hz, 2 F, m-F). iBuAl($C_6F_5$)$_2$ $^1H$ NMR ($C_6D_6$, 23° C.): δ1.89 (overlapping with the above structure, 1H, $Me_2CHCH_2$—), 0.99 (d, $J_{H–H}$=6.6 Hz, 6 H, $Me_2CHCH_2$—), 0.55 (s, br, 2 H, $Me_2CHCH_2$—). $^{19}F$ NMR ($C_6D_6$, 23° C.): δ121.74 (d, $^3J_{F–F}$=18.3 Hz, 2 F, o-F), −151.45 (t, $^3J_{F–F}$=20.9 Hz, 1F, p-F), −161.20 (tt, $^3J_{F–F}$=24.5 Hz, 2 F, m-F).

Example 2

In a glove box, FAAL (0.020 g, 0.032 mmol, toluene adduct) and di(isobutyl) (2,6-di-tert-butyl-4-methylphenoxy)aluminum (0.003 g, 0.008 mmol) were mixed in 0.7 mL of benzene-$d_6$ and the mixture was loaded into a NMR tube. NMR spectra were recorded after mixing these reagents in the NMR tube for 20 min. Two new species, isobutyl(pentafluorophenyl)(2,6-ditert-butyl-4-methylphenoxy)aluminum (iBu($C_6F_5$)Al(BHT)) and isobutylbis(pentafluorophenyl)aluminum (i-BuAl($C_6F_5$)$_2$), as well as a small amount of bis(pentafluorophenyl)(2,6-ditert-butyl-4-methylphenoxy)aluminum (($C_6F_5$)$_2$Al(BHT)) were found to form from the exchange reaction. No di(isobutyl)(2,6-di-tert-butyl-4-methylphenoxy)aluminum reagent remained. Residual FAAL reagent was also present.

iBu($C_6F_5$)Al(BHT) $^1H$ NMR ($C_6D_6$, 23° C.): δ7.10 (s, 2 H, Ar), 2.25 (s, 3 H, Ar-$CH_3$), 1.89 (septet, $J_{H–H}$=6.6 Hz, 1H, $Me_2CHCH_2$—), 1.50 (s, 18 H, tBu), 0.89 (d, $J_{H–H}$=6.6 Hz, 6 H, $Me_2CHCH_2$—), 0.50 (d, $J_{H–H}$=7.2 Hz, 2 H, $Me_2CHCH_2$—). $^{19}F$ NMR ($C_6D_6$, 23° C.): δ−120.93 (dd, $^3J_{F–F}$=18.3 Hz, 2 F, o-F), −149.65 (t, $^3J_{F–F}$=21.4 Hz, 1F, p-F), −159.61 (tt, $^3J_{F–F}$=24.5 Hz, 2 F, m-F). iBuAl($C_6F_5$)$_2$$^1H$ NMR ($C_6D_6$, 23° C.): δ1.89 (overlapping with the above structure, 1H, $Me_2CHCH_2$—), 0.99 (d, $J_{H–H}$=6.6 Hz, 6 H, $Me_2CHCH_2$—), 0.55 (s, br, 2 H, $Me_2CHCH_2$—). $^{19}F$ NMR ($C_6D_6$, 23° C.): δ−121.74 (d, $^3J_{F–F}$=18.3 Hz, 2 F, o-F), −151.45 (t, $^3J_{F–F}$=20.9 Hz, 1F, p-F), −161.20 (tt, $^3J_{F–F}$=24.5 Hz, 2 F, m-F). ($C_6F_5$)$_2$Al(BHT) $^1H$ NMR ($C_6D_6$, 23° C.): δ7.13 (s, 2 H, Ar), 2.28 (s, 3H, Ar-$CH_3$), 1.53 (s, 18 H, tBu). $^{19}F$ NMR ($C_6D_6$, 23° C.): δ−120.93(overlapping with other species, 2 F, o-F), −147.41 (t, $^3J_{F–F}$=21.4 Hz, 1F, p-F), −159.12 (tt, $^3J_{F–F}$=24.5 Hz, 2 F, m-F).

POLYMERIZATIONS

A 2-liter Parr reactor was used in the polymerizations. All feeds were passed through columns of alumina and a decontaminant (Q-5™ catalyst available from Englehardt Chemicals Inc.) prior to introduction into the reactor. Catalyst and cocatalysts are handled in a glovebox containing an atmosphere of argon or nitrogen.

A stirred 2.0 liter reactor is charged with about 740 g of mixed alkanes solvent and 118 g of 1-octene comonomer. Hydrogen is added as a molecular weight control agent by differential pressure expansion from a 75 ml addition tank at 25 psi (2070 kPa). The reactor is heated to the polymerization temperature of 130° C. and saturated with ethylene at 500 psig (3.4 MPa). FAAL is combined with diisobutyl(2,6-di(t-butyl)-4-methylphenoxy)aluminum as toluene solutions and allowed to stand at 25° C. for 15 minutes prior to use. Catalyst (t-butylamido)dimethyl(tetramethylcyclopentadienyl)silanetitanium 1,3-pentadiene) and the indicated cocatalyst, as dilute solutions in toluene, are mixed and transferred to a catalyst addition tank, and injected into the reactor. The polymerization conditions are maintained for 15 minutes with ethylene added on demand. The resulting solution is removed from the reactor, quenched with isopropyl alcohol, and stabilized by addition of 10 ml of a toluene solution containing approximately 67 mg of a hindered phenol antioxidant (Irganox™ 1010 from Ciba Geigy Corporation) and 133 mg of a phosphorus stabilizer (Irgafos 168 from Ciba Geigy Corporation).

Between polymerization runs a wash cycle in which 850 g of mixed alkanes is added to the reactor and the reactor heated to 150° C. The reactor is emptied of the heated solvent immediately before beginning a new polymerization run.

Polymers are recovered by drying in a vacuum oven set at 140° C. for about 20 hours. Density values are derived by determining the polymees mass when in air and when immersed in methylethylketone. Micro melt index values (MMI) are obtained using a "Custom Scientific Instrument Inc. Model CS-127MF-015" apparatus at 190° C. MMI (micro-melt index) are unit-less values calculated as follows: MMI=1/(0.00343 t -0.00251), where t=time in seconds. Results are contained in Table 1.

TABLE 1

| Run | Activator(s) | catalyst/activator** | ΔT*** (° C.) | Yield (g) | Efficiency g polymer/μg Ti | Density g/ml | MMI |
|---|---|---|---|---|---|---|---|
| 1 | FAAL/Dibal-Bot | 1/4/1 | 36.8 | 71.6 | 1.50 | 0.902 | 5.6 |
| 2 | FAAL/Dibal-Bot | 0.25/1/0.25 | 8.6 | 57.8 | 4.83 | 0.899 | 2.5 |
| A* | B(C$_6$F$_5$)$_3$ | 1.5/1.5 | 6.0 | 85.5 | 1.19 | 0.898 | 4.2 |
| B* | FAAL | 0.5/0.5 | 0.0 | 0.9 | 0.038 | — | — |

*comparative example, not an example of the invention.
**Catalyst ratios reflect μmole metal complex/μmole first activator/μmole second activator
***exotherm Propylene Homopolymerization The above polymerization conditions were substantially repeated excepting that about 250 g of mixed alkanes solvent and 300 g of propylene are polymerized at a polymerization temperature of 70° C.

The cocatalyst was prepared by combining FAAL with diisobutyl(2,6-di-tert-butyl-4-methylphenoxy)aluminum and allowing the mixture to stand at 25° C. for 15 minutes. The mixture was not devolatilized to remove triisopropylborane byproducts. Catalyst, dimethylsilanebis(2-methyl-4-phenylindenyl)zirconium 1,4-diphenyl-1,3-butadiene and the indicated cocatalyst, as dilute solutions in toluene, are then mixed at the indicated ratio (zirconium complex: FAAL: DIBAL-BOT), transferred to a catalyst addition tank, and injected into the reactor. The polymerization conditions are maintained for 15 minutes. Results are contained in Table 2.

TABLE 2

| Run | Activator(s) | catalyst/activator** | Yield (g) | Efficiency (g polymer/μg Zr) |
|---|---|---|---|---|
| 3 | FAAL/DIBAL-BOT | 0.25/1/0.25 | 91.9 | 4.03 |
| 4 | " | 0.25/0.5/0.125 | 82.7 | 3.25 |
| 5 | " | 0.125/0.5/0.125 | 80.0 | 7.02 |
| 6 | " | 0.125/0.25/0.125 | 37.1 | 3.25 |
| D* | B(C$_6$F$_5$)$_3$ | 2.5/2.5 | 31.3 | 0.14 |

*comparative example, not an example of the invention.
**catalyst ratios, μmole metal complex/μmole first activator/μmole second activator Example 3

In a glove box, FAAL (0.032 mmol, toluene adduct) and dibal-bot (0.008 mmol) mixed in 0.7 mL of benzene-d$_6$ and the mixture was loaded into a NMR tube. All species in the mixture were identified as being the same as in Example 1. The metal complex, (t-butylamido) (tetramethylcyclopentadienyl)-dimethylsilanetitanium dimethyl, (8 μmol) was added to the above solution and the resulting mixture immediately turned to an orange color. NMR spectroscopic features of the major product are consistent with a μ-bridged bisadduct of the formula Me$_2$Si(η$^5$-Me$_4$C$_5$)(t-BuN)Ti[(μ-Me)Al(C$_6$F$_5$)$_3$]$_2$.

Example 4

In a glove box, FAAL (0.032 mmol, toluene adduct) and dibal-bot (0.008 mmol) were mixed in 0.7 mL of benzene-d$_6$ and the mixture was loaded into a NMR tube. All species in the mixture were identified as the same as in Example 1. The complex (rac-dimethylsilyl-bis(1-indenyl)zirconium dimethyl, 8 μmol) was added to the above solution whereupon the resulting mixture immediately turned to deep red color. NMR spectroscopic features of the major product are consistent with a μ-bridged bisadduct of the formula: rac-Me$_2$Si(η$^5$-Ind)$_2$Zr[(μ-Me)Al(C$_6$F$_5$)$_3$]$_2$.

What is claimed is:

1. A composition comprising:

A) an aluminum compound corresponding to the formula AlAr$^f_3$, where

Ar$^f$ is a fluorinated aromatic hydrocarbyl moiety of from 6 to 30 carbon atoms; and B) an aluminum compound corresponding to the formula: AlAr$^f$Q$^1$Q$^2$, or a dimer, adduct, or mixture thereof, where:

Ar$^f$ is as previously defined;

Q$^1$ is Ar$^f$ or a C$_{1-20}$ hydrocarbyl group, optionally substituted with one or more cyclohydrocarbyl, hydrocarbyloxy, hydrocarbylsiloxy, hydrocarbylsilylamino, hydrocarbylsilyl, silylhydrocarbyl, di(hydrocarbylsilyl)amino, hydrocarbylamino, di(hydrocarbyl)amino, di(hydrocarbyl)phosphino, or hydrocarbylsulfido groups having from 1 to 20 atoms other than hydrogen, or, further optionally, such substituents are covalently bonded to each other to form one or more fused rings or ring systems; and $Q^2$ is an aryloxy, arylsulfido or di(hydrocarbyl)amido group, optionally substituted with one or more hydrocarbyl, cyclohydrocarbyl, hydrocarbyloxy, hydrocarbylsiloxy, hydrocarbylsilylamino, hydrocarbylsilyl, silylhydrocarbyl, di(hydrocarbylsilyl)amino, hydrocarbylamino, di(hydrocarbyl)amino, di(hydrocarbyl)phosphino, or hydrocarbylsulfido groups having from 1 to 20 atoms other than hydrogen, or, further optionally such substituents are covalently bonded to each other to form one or more fused rings or ring systems, said $Q^2$ having from 3 to 20 atoms other than hydrogen; and the molar ratio of A):B) in the composition is from 0.1:1 to 10:1.

2. A composition comprising:

A) an aluminum compound corresponding to the formula $AlAr^f_3$, where $Ar^f$ is a fluorinated aromatic hydrocarbyl moiety of from 6 to 30 carbon atoms;

B) an aluminum compound corresponding to the formula: $AlAr^fQ^1Q^2$, or a dimer, adduct, or mixture thereof; where:

$Ar^f$ is as previously defined;

$Q^1$ is $Ar^f$ or a $C_{1-20}$ hydrocarbyl group, optionally substituted with one or more cyclohydrocarbyl, hydrocarbyloxy, hydrocarbylsiloxy, hydrocarbylsilylamino, hydrocarbylsilyl, silylhydrocarbyl, di(hydrocarbylsilyl)amino, hydrocarbylamino, di(hydrocarbyl)amino, di(hydrocarbyl)phosphino, or hydrocarbylsulfido groups having from 1 to 20 atoms other than hydrogen, or, further optionally, such substituents are covalently bonded to each other to form one or more fused rings or ring systems;

$Q^2$ is an aryloxy, arylsulfido or di(hydrocarbyl)amido group, optionally substituted with one or more hydrocarbyl, cyclohydrocarbyl, hydrocarbyloxy, hydrocarbylsiloxy, hydrocarbylsilylamino, hydrocarbylsilyl, silylhydrocarbyl, di(hydrocarbylsilyl)amino, hydrocarbylamino, di(hydrocarbyl)amino, di(hydrocarbyl)phosphino, or hydrocarbylsulfido groups having from 1 to 20 atoms other than hydrogen, or, further optionally such substituents are covalently bonded to each other to form one or more fused rings or ring systems, said $Q^2$ having from 3 to 20 atoms other than hydrogen; and C) an aluminum exchange compound or mixture thereof, in the aggregate corresponding to the formula, $AlAr^f_2Q^1$, where $Q^1$ is not $Ar^f$, the molar ratio of A):B):C) in the composition is from 0.1:1.0:0.001 to 10.0:1.0:1.0.

3. A composition according to claim 1 or 2 where $Ar^f$ is pentafluorophenyl, $Q^1$ is isopropyl or isobutyl, and $Q^2$ is 4-methyl-2,6-di-t-butylphenoxy or bis(trimethylsilyl)amido.

4. A composition according to claim 1 or 2 wherein $Ar^f$ is perfluoroaryl, $Q^1$ is $C_{3-6}$ alkyl containing at least one secondary or tertiary carbon center and $Q^2$ is aryloxy or dialkylamido of up to 10 carbons.

* * * * *